United States Patent
Callahan

(10) Patent No.: US 10,441,410 B2
(45) Date of Patent: Oct. 15, 2019

(54) ACCOMMODATIVE INTRAOCULAR LENS THAT EJECTS POST CAPSULAR OPACIFICATION AND SELF-CENTERS

(71) Applicant: Wayne B. Callahan, Abingdon, VA (US)

(72) Inventor: Wayne B. Callahan, Abingdon, VA (US)

(*) Notice: Subject to any disclaimer, the term of this patent is extended or adjusted under 35 U.S.C. 154(b) by 294 days.

(21) Appl. No.: 15/293,630

(22) Filed: Oct. 14, 2016

(65) Prior Publication Data

US 2018/0104047 A1     Apr. 19, 2018

(51) Int. Cl.
A61F 2/16       (2006.01)

(52) U.S. Cl.
CPC ........... *A61F 2/1618* (2013.01); *A61F 2/164* (2015.04); *A61F 2002/169* (2015.04); *A61F 2002/1682* (2015.04)

(58) Field of Classification Search
CPC ........ A61F 2/1648; A61F 2/1613; A61F 2/16; A61F 2/1694; A61F 2002/1682; A61F 2002/1689; A61F 2002/169
See application file for complete search history.

(56) References Cited

U.S. PATENT DOCUMENTS

| | | | |
|---|---|---|---|
| 4,571,039 A * | 2/1986 | Poler | A61F 9/0017 351/159.21 |
| 4,863,463 A * | 9/1989 | Tjan | A61F 2/16 623/6.42 |
| 5,366,501 A * | 11/1994 | Langerman | A61F 2/1694 623/6.42 |
| 5,496,366 A | 3/1996 | Cumming | |

(Continued)

FOREIGN PATENT DOCUMENTS

| | | | |
|---|---|---|---|
| FR | 2728458 | * | 6/1996 |
| FR | 2728459 | * | 6/1996 |
| FR | 2770394 | * | 10/1997 |

OTHER PUBLICATIONS

"PCO still a major hurdle in successful cataract surgery", Ocular Surgery News U.S. Edition, Jul. 25, 2011.
Abhay R Vasavada; Shetal M Raj; Gauri D Shah; Mayank a Nanavaty, "Posterior Capsule Opacification After Lens Implantation", Expert Rev Ophthalmol. 2013;8(2):141-149.

(Continued)

*Primary Examiner* — David H Willse
*Assistant Examiner* — Tiffany P Shipmon
(74) *Attorney, Agent, or Firm* — New River Valley IP Law, P.C.; Michele L. Mayberry

(57) ABSTRACT

Described is an accommodating intraocular lens with a bi-convex, bi-aspheric, smooth surfaced optic held inside an anterior annulus via tabs. A second larger diameter annulus is positioned posteriorly and connects via a sloped surface to where the annuluses are at a maximum separation when viewing NEAR objects and minimum separation in the FAR position. The sloped surface is cut into ribbons, tabs and/or other annuluses without pushing the surfaces into the capsule when implanted; therefore, only the anterior and posterior annuluses have a force component against the capsule. The proximal edge of the anterior annulus is anterior to the apex of the anterior surface of the optic. The anterior capsule resting on the annulus leaves space for hydration of the capsule and reduces potential warpage of the optic. The annulus edge is designed to scrape posterior capsular opacification from the capsule.

20 Claims, 14 Drawing Sheets

(56) References Cited

U.S. PATENT DOCUMENTS

| | | | |
|---|---|---|---|
| 6,932,839 | B1 | 8/2005 | Kamerling et al. |
| 7,029,497 | B2 | 4/2006 | Zhang et al. |
| 7,662,180 | B2 | 2/2010 | Paul et al. |
| 7,763,069 | B2 | 7/2010 | Brady et al. |
| 7,806,929 | B2 | 10/2010 | Brown |
| 7,871,437 | B2 | 1/2011 | Hermans et al. |
| 8,034,107 | B2 | 10/2011 | Stenger |
| 8,377,125 | B2 | 2/2013 | Kellan |
| 8,523,942 | B2 | 9/2013 | Cumming |
| 9,084,674 | B2 | 7/2015 | Brady et al. |
| 2004/0236423 | A1* | 11/2004 | Zhang .................. A61F 2/1613 623/6.37 |
| 2006/0155373 | A1* | 7/2006 | Israel ..................... A61F 2/16 623/6.4 |

OTHER PUBLICATIONS

Andres Bernal, Jean-Marie Parel, and Fabrice Manns, "Evidence for Posterior Zonular Fiber Attachment on the Anterior Hyaloid Membrane", IOVS Nov. 2006 vol. 47 No. 11, 4708-4713.

D. Jackson Coleman, "On the Hydraulic Suspension Theory of Accommodation", Transactions of the American Ophthalmological Society vol. LXXXIV 1986, 846-868.

J W Rohen, "Scanning electron microscopic studies of the zonular apparatus in human and monkey eyes", Investigative Ophthalmology & Visual Science Feb. 1979, vol. 18, 133-144.

Michela Cimberle, "More than 2,000 CrystaLens IOLs implanted worldwide" Ocular Surgery News U,S. Edition, Aug. 15, 2002.

R.A. Moses, "Detachment of cilary body- anatomical and physical considerations", Investigative Ophthalmology, 1965, 4(5): 935-941.

\* cited by examiner

ACCOMMODATIVE INTRAOCULAR LENS THAT EJECTS POST CAPSULAR OPACIFICATION AND SELF-CENTERS

BACKGROUND OF THE INVENTION

Field of the Invention

The present invention relates generally to intraocular lenses and more specifically to an accommodating intraocular lens having a haptic comprising two or more annuluses connected together by one or more ribbons or tabs. The ribbons are disposed in parallel to the annuluses while the tabs are disposed radially to the annuluses. Together, the ribbons and tabs provide a spring-like capability to the haptic such that the annuluses are at a maximum separation when viewing NEAR objects and minimum separation when viewing FAR objects. The intraocular lens is useful for replacing natural lenses diseased by cataracts and other conditions.

Description of Related Art

Anatomy

FIG. 1 shows the clear portion of the eye, cornea (1), and functions as the window to the remainder of the eye and refracts (bends) light. Just behind the cornea is the anterior chamber (2) filled with a clear watery, salty liquid (aqueous humor). At the back of the anterior chamber is the colored iris (4); having an opening, pupil (3), which changes size regulating the amount of light passing into the eye. The cornea and white portion of the eye, sclera (10), meet at a point defined as the limbus (7). The most distal point from the prime meridian of the iris attaches just in front of the limbus. Much of the ciliary body (6) is attached to the sclera. The inside surface of the sclera is attached to the choroid (12). A study by Moses (see R. A. Moses, "Detachment of cilary body-anatomical and physical considerations", Investigative Ophthalmology, 1965, 4(5): 935-941) implicated even in dead eyes the choroid is under tension and in all sectors has elasticity similar to soft rubber with a significant tensile strength. It is well known that while the cornea will collapse during cataract surgery, the sclera maintains its dome shape. The lamellar (11) tissue holds the choroid and sclera tissues together. The retina (13) attaches to the choroid and is a delicate light-sensitive membrane lining the inner eyeball and connected by the optic nerve to the brain. The space between the natural lens and the retina (13) is filled with vitreous humor (14), a clear jelly-like substance. The posterior chamber (5) is the space between the iris (4) and anterior capsule (17) of the natural (crystalline) lens (16). The anterior zonule fibers (8) and the posterior zonule fibers (9) are fine hair-like structures that attach to the ciliary body (6) with the opposite ends attached to the natural lens. From ultrasound data it is estimated the length of the zonules outside the ciliary body to be about 1.4 millimeters (mm) for the anterior and 2.3 mm for the posterior. Nutrimental aqueous is processed by the ciliary body for use by the optical surfaces without blood vessels, which include the cornea and natural lens. The anterior zonule fibers (8) attach (18) very near the end of the anterior capsule (17). The opposite ends extend into the ciliary body (6) where the anterior zonules terminate very close to the point where the iris (4) attaches to the cornea (1).

As shown in FIG. 2, the posterior zonules attach (20) more tangentially to the posterior capsule (19) with the opposite end extending into the ciliary body and arching toward the choroid (12). Pictures (see J W Rohen, "Scanning electron microscopic studies of the zonular apparatus in human and monkey eyes", Investigative Ophthalmology & Visual Science February 1979, Vol. 18, 133-144 ("Rohen, 1979")) and cadaver reviews have shown the zonules are not just loose fibers, but are woven into mat or carpet appearance, which adds considerable strength. The fibers are firmly attached to the ciliary processes. The outer shell of the natural (crystalline) lens capsule (16) is a smooth, thin, transparent, delicate layer of connective tissue. In younger people when the ciliary body (6) increases in size, removing tension, the natural lens assumes a more globular shape as desired for NEAR vision (see Rohen, 1979).

As can be seen by the FIG. 3, when looking at FAR objects the ciliary body reduces in size adding tension to the zonules and stretching the natural lens capsule to a flatter shape (22). Inside the anterior portion of the natural lens capsule the epithelium pumps nutrients and fluids from the aqueous into the cavity. Throughout life the lens epithelium generates lens fibers that make up the bulk of the lens mass. They are long, thin, transparent cells which are typically 4 to 7 microns in diameter and up to 12 mm long. In young eyes the fibers can be positioned from the anterior to the posterior pole. The bunching of the fibers gives the appearance of a laminar assembly with the index of refraction varying from 1.4064 at the prime meridian to 1.3864 near the distal ends of the natural lens. The polar circumference of the natural lens is the arc distance of the anterior capsule plus the arc distance of the posterior capsule plus twice the arc distance of the equatorial region. It is well known in the industry when implanting intraocular lenses that are shaped like a coin (relatively flat disc lens) the diameter of the lenses should be approximately 10.5 mm; therefore, the arc circumference of the natural lens capsule must be twice the 10.5 mm plus an allowance for the edge thickness. Many believe the fibers generated by the natural lens anterior capsule epithelium move toward the posterior capsule depositing between the soft material (cortex) of the posterior capsule and the last layer of fibers with the process continuing until the natural lens capsule becomes too large to change shape. More logically as the person ages the fibers do not have enough energy to force their way between the posterior capsule and previous fibers and must remain in the equatorial area. The extra fibers prevent the capsule from assuming the full NEAR position (21); therefore, the amount of accommodation is reduced. Over time the density of the fibers increase until a cataract is formed. Coleman (see D. Jackson Coleman, "On the Hydraulic Suspension Theory of Accommodation", Transactions of the American Ophthalmological Society Vol. LXXXIV 1986, "Coleman, 1986") and Bernal, Parel, and Manns (see Andres Bernal, Jean-Marie Parel, and Fabrice Manns, "Evidence for Posterior Zonular Fiber Attachment on the Anterior Hyaloid Membrane", IOVS November 2006 Volume 47 No. 11) discussed a ring (hyaloid membrane) that is sheets of condensation within the vitreous. The membrane attaches to the ora serrata, which is the edge of the retina located about 6.5 mm behind the corneo-scleral junction (limbus). The membrane attaches to the back of the natural lens including the woven zonular fibers and adds strength creating a pressure differential diaphragm between the vitreous and aqueous cavities. It is well known in the industry and concluded by Coleman that during accommodation the natural lens gets thicker along the plane of the prime meridian and thinner distally from the prime meridian. Coleman's work concluded the pressure in the vitreous is slightly higher than the pressure in the aqueous during NEAR vision and the reverse for FAR vision; however, the differential pressure of the vitreous between readings was slight. The volume of the vitreous cavity is significantly larger than the aqueous cavity; therefore, a given amount of aqueous volume change would give a significantly larger change in pressure in the aqueous than the vitreous. There will be a positive force pushing anteriorly on the natural lens or an implanted intraocular lens when the eye is looking at NEAR objects and a positive force pushing posteriorly when the eye is looking at FAR objects.

Accommodation

It is readily accepted as shown in FIG. 4 that distant objects (FAR) assume the rays to be parallel light (23) with the object at infinity. For reading or looking at closer work it is assumed the light is taken from a point light (24), the point is not to scale. The corneal refraction is approximately the same. Since the light rays need to arrive at or near the fovea (15), the natural lens changes shape making the structure more globular. As explained by Coleman (see Coleman, 1986) the ciliary processes relax the natural lens in the NEAR position and add tension in the FAR position stretching the natural lens into a more flattened shape. In both the NEAR and FAR positions corneal refraction (25) accounts for approximately ⅔rds of the desired refraction. The light travels from the cornea through the pupil to the natural lens anterior surface where the rays are refracted (26) then travel to the posterior surface, which again refracts (27) the light coming to a point on or near the fovea (15).

Intraocular lenses for FAR vision and multi-focal lenses for NEAR vision are readily available. One older model is shown in FIG. 5 with thin angulated haptics which are spring like extensions of the optic. From tip to tip the lenses are normally 11.2 mm to 12.5 mm with some even larger, which distorts the capsule and stretches it to an almost flat surface leaving little movement for accommodation. Multi-focal lenses by definition have multiple images creating glare. Professionals in the field are striving for perfection, yet to achieve the desired outcome posterior capsular opacification (PCO) must be reduced to a level that does not impede the vision of the patient. A perfect lens would allow a safe effective intraocular lens implantation when a person first needed reading spectacles and would provide almost perfect vision for the remainder of their life.

Posterior Capsular Opacification, PCO

After cataract surgery the inside surfaces (epithelium) of the natural lens anterior surfaces continue to generate cells, which migrate toward the posterior surface of the capsule. Earlier lens models had rounded edges allowing the fibers to easily penetrate between the posterior surface of the lenses and the capsule impeding vision and contrast sensitivity. This is Posterior Capsular Opacification, PCO. Models with sharp edges delay the visual effects of PCO; however, with time the fibers grow in front of the optic reducing vision. Historically haptics spring like structures position the optic within the capsule. The spring effect stretches the capsule forcing it to become almost flat. Some haptic designs retard the growth of PCO in quadrants where the haptics are present; yet, capsule remnants and an edge of a haptic often form a tunnel that can accelerate the movement of the cells directly to the edge of the optic. To obtain long term satisfactory results PCO must be blocked in all directions. When intraocular lenses stretch the capsule remnants tightly little aqueous can reach the inside surfaces leaving an unhealthy capsule. Three dimensional intraocular lenses are being developed and may stretch the equatorial region until the area resembles a continuation of the posterior and anterior surfaces. Such lenses can reduce the tendency for PCO collection in the equatorial region; however, PCO still collects in other places, especially near the contact area between the lens and the posterior capsule. If designed for good aqueous flow inside the natural lens cavity three dimensional lenses can contribute to healthier lens capsules. It has recently been reported that if the PCO particles are separated from the tissue and saturated with aqueous they will not reattach and can be carried out of the eye through the natural aqueous process. The treatment of PCO also involves a risk to the eye, and therefore, it is important that strategies to retard and prevent PCO may contribute to preserving visual acuity in patients over their lifetimes. According to an article by Abhay R Vasavada and others, "capsular opacification, in particular PCO, still remains a physiological complication of uneventful cataract surgery" (see Abhay R Vasavada; Shetal M Raj; Gauri D Shah; Mayank A Nanavaty. Posterior Capsule Opacification After Lens Implantation", Expert Rev Ophthalmol. 2013; 8(2): 141-149) Methods currently available cannot significantly decrease the rate of PCO. The quest for its eradication is ongoing. Related efforts in this area include those described in U.S. Pat. Nos. 9,084,674; 8,523,942; 8,034,107; 7,871, 437; 8,377,125; 7,806,929; 7,763,069; 7,662,180; 6,932, 839; and 5,496,366. Yet, there remains a need in the art for an intraocular lens that addresses this issue.

SUMMARY OF THE INVENTION

Embodiments of the invention provide an accommodating intraocular lens with a bi-convex, bi-aspheric, smooth surfaced optic held inside an anterior annulus via tabs. A second larger diameter posterior annulus is positioned posteriorly and connects via a sloped surface to where the annuluses are at a maximum separation when viewing NEAR objects and minimum separation in the FAR position. The sloped surface is cut into ribbons, tabs and/or additional annuluses without pushing the surfaces into the capsule when implanted; therefore, only the anterior and posterior annuluses have a force component against the capsule. The proximal edge of the anterior annulus is anterior to the apex of the anterior surface of the optic. The anterior capsule resting on the anterior annulus leaves space for hydration of the capsule. It also reduces potential warpage of the optic. The anterior annulus edge is designed to scrape PCO from the capsule. When changing accommodative states, aqueous turbulence will increase the removal of PCO. The posterior annulus and capsule squeeze PCO when moving from the FAR to NEAR positions. Once saturated with aqueous fluid the PCO can be carried out of the eye via natural physiological processes.

In embodiments, the annuluses are held together via tabs attached to ribbons which are cut into the haptic slope forming the equivalent of complex cantilevered beams. The ribbons can be parallel to (or concentric with—depending on whether the device is in a relaxed or compressed state) the anterior and posterior annuluses or angled. The tabs can also be attached to additional annuluses. When the intraocular lens is implanted, the anterior and posterior annuluses in contact with the segments of the capsule stretch each segment tight. With tight capsular segments and differential pressures the vitreous pressure is higher than the aqueous for NEAR vision and the reverse for distant vision. The differential pressures allow the optic to be held in position. If the surgeon refracts the patient slightly hyperopic the optic is expected to stop at emmetropia. For lenses manufactured with stiffer materials, the lens can be squeezed until collapsed and expected to remain in such a state long enough for implantation using only forceps. Forces placed on the anterior and posterior annuluses via capsule remnants will force centration of the lens without surgical assistance.

Specific aspects of the invention include Aspect 1, which provides an intraocular lens with an optic placed inside an anterior annulus and having a posterior annulus that is larger in diameter than the anterior annulus, wherein the annuluses are connected by way of a haptic slope surface that is sloped to where the annuluses are at a maximum separation along a plane perpendicular to the radii of the annuluses when viewing NEAR objects and collapsed to where the anterior annulus rests inside or near the posterior annulus when viewing FAR objects.

According to Aspect 2, the lens as in Aspect 1 is provided where the components connecting the anterior and posterior annuluses are in different planes parallel to the prime meridian and do not have a force component in a plane that will place force on the capsule during movement.

Aspect 3 is the lens in either of Aspects 1 and 2 where the optic is bi-convex.

Aspect 4 is the lens in any one of Aspects 1-3 where the optic is bi-aspheric with smooth surfaces that can vary in power to reduce the profile of the lens to allow more travel space for accommodation.

Aspect 5 is the lens in any one of Aspects 1-4 where the anterior annulus and the optic are held together via a series of attachment tabs.

Aspect 6 is the lens in any one of Aspects 1-5 where the anterior annulus has a point that is anterior to the apex of the optic.

Aspect 7 is the lens in any one of Aspects 1-6 where the anterior capsule rest against the apex of the anterior annulus preventing warpage of the optic.

Aspect 8 is the lens in any one of Aspects 1-7 where the space between the tabs allows hydration of the natural lens capsule.

Aspect 9 is the lens in any one of Aspects 1-8 where the anterior annulus proximal edge scrapes some PCO free allowing saturation with aqueous and removal from the eye via normal physiological processes.

Aspect 10 is the lens in any one of Aspects 1-9 where changing accommodative state creates aqueous turbulence placing PCO into the aqueous for saturation.

Aspect 11 is the lens in any one of Aspects 1-10 where the posterior annulus rest over the posterior zonular-capsular junction.

Aspect 12 is the lens in any one of Aspects 1-11 where PCO is trapped between the posterior annulus and the posterior capsule.

Aspect 13 is the lens in any one of Aspects 1-12 where the annuluses are held together by ribbons.

Aspect 14 is the lens in any one of Aspects 1-13 where the ribbons are located along the haptic slope.

Aspect 15 is the lens in any one of Aspects 1-14 where the ribbons are a series of cantilevered beams.

Aspect 16 is the lens in any one of Aspects 1-15 where the cantilevered beams function as a complex spring.

Aspect 17 is the lens in any one of Aspects 1-16 where the anterior and posterior annuluses are held together by additional annuluses.

Aspect 18 is the lens in any one of Aspects 1-17 where the annuluses are connected by tabs.

Aspect 19 is the lens in any one of Aspects 1-18 where the anterior capsule is stretched tightly over the anterior annulus.

Aspect 20 is the lens in any one of Aspects 1-19 where the posterior capsule is stretched tightly over the posterior annulus.

Aspect 21 is the lens in any one of Aspects 1-20 where when in the NEAR position, the vitreous force is greater than the aqueous force aiding the movement or holding the lens in the NEAR position.

Aspect 22 is the lens in any one of Aspects 1-21 where when stress is added to the zonules by the ciliary body the optic and anterior annulus collapse forcing the optic posteriorly.

Aspect 23 is the lens in any one of Aspects 1-22 where when in the FAR position the aqueous force is greater than the vitreous force holding the lens in the FAR position.

Aspect 24 is the lens in any one of Aspects 1-23 where any remaining PCO is collected along the posterior capsule and the outside of the posterior annulus, which can form a PCO annulus.

Aspect 25 is the lens in any one of Aspects 1-24 where when moving toward NEAR vision the posterior capsule squeezes the PCO against the posterior annulus ejecting PCO into the aqueous.

Aspect 26 is the lens in any one of Aspects 1-25 where the surgeon refracts the patient slightly hyperopic allowing the force on the capsule to stop movement at emmetropia for FAR vision.

Aspect 27 is the lens in any one of Aspects 1-26 where when manufactured with a relatively stiff material the lens can be squeezed and implanted using only forceps and allowed to open slowly after implantation.

Aspect 28 is the lens in any one of Aspects 1-27 where anatomical capsular forces on the anterior and posterior annuluses will move the lens until centration is achieved.

Aspect 29 is an intraocular lens comprising: an optic; and a haptic supporting the optic and comprising an outer annulus and an inner annulus, wherein the outer annulus has a larger radius than a radius of the inner annulus.

Aspect 30 is the intraocular lens of Aspect 29, wherein the inner annulus is in communication with the optic by way of a plurality of tabs.

Aspect 31 is the intraocular lens of Aspect 29 or 30, wherein the inner annulus is in communication with the outer annulus by way of a plurality of tabs and/or a plurality of ribbons and/or a plurality of intermediate annuluses.

Aspect 32 is the intraocular lens of any of Aspects 29-31, wherein the inner annulus is in communication with the outer annulus by way of a plurality of tabs and a plurality of ribbons, wherein each of the ribbons comprises an arcuate bend.

Aspect 33 is the intraocular lens of any of Aspect 32, wherein the arcuate bend is a 180 degree bend.

Aspect 34 is the intraocular lens of any of Aspects 29-33, wherein the haptic is flexible and capable of disposing the optic in any position between the inner annulus and the outer annulus.

Aspect 35 is the intraocular lens of any of Aspects 29-34, wherein the inner annulus is in communication with the outer annulus by way of at least one intermediate annulus, and tabs connecting the inner annulus to the at least one intermediate annulus, and tabs connecting the at least one intermediate annulus to the outer annulus.

Aspect 36 is the intraocular lens of any of Aspects 29-35, wherein the at least one intermediate annulus comprises two intermediate annuluses.

Aspect 37 is the intraocular lens of any of Aspects 29-36, wherein the haptic slopes outwardly from the inner annulus to the outer annulus.

Aspect 38 is an intraocular lens comprising: an optic; a haptic in communication with the optic, comprising: a first annulus; a second annulus; a plurality of tabs connecting the optic and the annuluses; wherein a cross-section of the intraocular lens along a plane perpendicular to a diameter of the intraocular lens reveals that the haptic is sloped.

Aspect 39 is the intraocular lens of Aspect 38, wherein the haptic is flexible and capable of disposing the optic in any position between the first annulus and the second annulus.

Aspect 40 is the intraocular lens of any of Aspects 38-39, wherein the first annulus is in communication with the second annulus by way of at least one intermediate annulus, and tabs connecting the first annulus to the at least one intermediate annulus, and tabs connecting the at least one intermediate annulus to the second annulus.

Aspect 41 is an intraocular lens comprising: an optic; a flexible haptic comprising a network of annuluses and tabs configured to provide flexibility to the haptic from a compressed state to a relaxed state; wherein when the haptic moves from a relaxed state to a compressed state, the annuluses are capable of moving toward one another; and wherein when the haptic moves from a compressed state to a relaxed state, the annuluses are capable of moving away from one another.

Aspect 42 is the intraocular lens of Aspect 41, wherein during use by a subject the annuluses and tabs function as a spring such that the annuluses are at a maximum separation when the subject is viewing near objects and at a minimum separation when the subject is viewing far objects.

Aspect 43 is the intraocular lens any of Aspects 29-42, wherein the optic is bi-convex or wherein the optic is bi-aspheric.

Additional aspects include Aspect 44, which provides an intraocular lens comprising an optic, a haptic comprising at least a first and second annulus concentrically disposed and surrounding the optic, wherein the first annulus has a radius that is greater than a radius of the second annulus.

Aspect 45 is the intraocular lens of Aspect 44, wherein at least one of the annuluses is in communication with the optic by way of a plurality of tabs disposed radially to the annuluses.

Aspect 46 is the intraocular lens of either of Aspect 44 or 45, wherein at least the first and second annulus are in communication with each other by way of a plurality of tabs disposed radially to the annuluses and/or ribbons disposed concentrically to the annuluses.

Aspect 47 is the intraocular lens of any one of Aspects 44-46, wherein each of the ribbons comprises a first portion concentrically disposed to a second portion, wherein the first portion and second portion are in communication with each other by way of an arcuate bend and form a cantilevered structure.

Aspect 48 is the intraocular lens of any one of Aspects 44-47, wherein the first ribbon portion and second ribbon portion are concentrically disposed between the first and second annulus.

Aspect 49 is the intraocular lens of any one of Aspects 44-48, wherein the first annulus and second annulus are in communication with the ribbons by way of one or more tabs disposed radially to the ribbons and annuluses.

Aspect 50 is the intraocular lens of any one of Aspects 44-49, comprising at least a third annulus, wherein the first, second, and third annulus are concentrically disposed and surrounding the optic and in communication with each other by way of a plurality of tabs disposed radially to the annuluses.

Aspect 51 is the intraocular lens of any one of Aspects 44-50, comprising at least a fourth annulus, wherein the first, second third, and fourth annuluses are concentrically disposed and surrounding the optic and in communication with each other by way of a plurality of tabs disposed radially to the annuluses.

Aspect 52 is the intraocular lens of any one of Aspects 44-51, wherein a cross-section of the intraocular lens through a lens diameter reveals that the haptic is sloped at an acute angle relative to the optic.

Aspect 53 is the intraocular lens of any one of Aspects 44-52, wherein the optic is bi-convex.

Aspect 54 is the intraocular lens of any one of Aspects 44-53, wherein the optic is bi-aspheric.

Aspect 55 is the intraocular lens of any one of Aspects 44-54, wherein the optic has a circumference that is disposed in a first plane and at least one of the annuluses has a circumference that is disposed in a different plane that is in parallel relative to the first plane.

Aspect 56 is the intraocular lens of any one of Aspects 44-55, wherein the first annulus has a circumference disposed in a first plane and the second annulus has a circumference that is disposed in a second plane that is in parallel relative to the first plane.

Aspect 57 is the intraocular lens of any one of Aspects 44-56 wherein the ribbons form a cantilevered structure.

Aspect 58 is the intraocular lens of any one of Aspects 44-57, wherein the arcuate bend is a 180 degree bend.

Aspect 59 is an intraocular lens comprising an optic, a haptic in communication with and surrounding the optic, comprising a first annulus having a first radius, a second annulus having a second radius, a series of tabs and/or cantilevered structures disposed between and in communication with the first annulus and the second annulus, wherein the first radius is greater than the second radius, wherein a cross-section of the intraocular lens through a lens diameter reveals that the haptic is sloped at an acute angle.

Aspect 60 is an intraocular lens comprising an optic, a haptic comprising at least a first and second annulus, and a series of tabs and/or bands in communication with the annuluses, wherein the first annulus has a radius that is greater than a radius of the second annulus; wherein the tabs are disposed radially to the annuluses and/or bands are disposed concentrically to the annuluses.

Aspect 61 is the intraocular lens of Aspect 60, wherein two adjacent bands are in communication with each other by way of an arcuate bend at one end, forming a cantilevered structure.

Aspect 62 is an intraocular lens comprising an optic, a haptic comprising a network of annuluses, tabs, and bands, wherein the annuluses and bands are disposed concentrically surrounding the optic and the tabs are disposed radially to the annuluses and bands, wherein each annulus has a circumference, and wherein each annulus circumference is disposed in a different plane and is greater than a circumference of an adjacent annulus.

Aspect 63 is the intraocular lens of Aspect 62, wherein two adjacent bands are in communication with each other by way of an arcuate bend at one end, forming a cantilevered structure.

Aspect 64 is the intraocular lens of Aspect 44, wherein during use the ribbons and tabs function as a complex spring such that the first and second annuluses are at a maximum separation when viewing near objects and minimum separation when viewing far objects.

Aspect 65 is the intraocular lens of Aspect 60, wherein during use the bands and tabs function as a complex spring such that the first and second annuluses are at a maximum separation when viewing near objects and minimum separation when viewing far objects.

Aspect 66 is the intraocular lens of Aspect 62, wherein during use the bands and tabs function as a complex spring such that the first and second annuluses are at a maximum separation when viewing near objects and minimum separation when viewing far objects.

BRIEF DESCRIPTION OF THE DRAWINGS

The accompanying drawings illustrate certain aspects of embodiments of the present invention, and should not be used to limit the invention. Together with the written description the drawings serve to explain certain principles of the invention.

DETAILED DESCRIPTION OF VARIOUS EMBODIMENTS OF THE INVENTION

Figure 1:
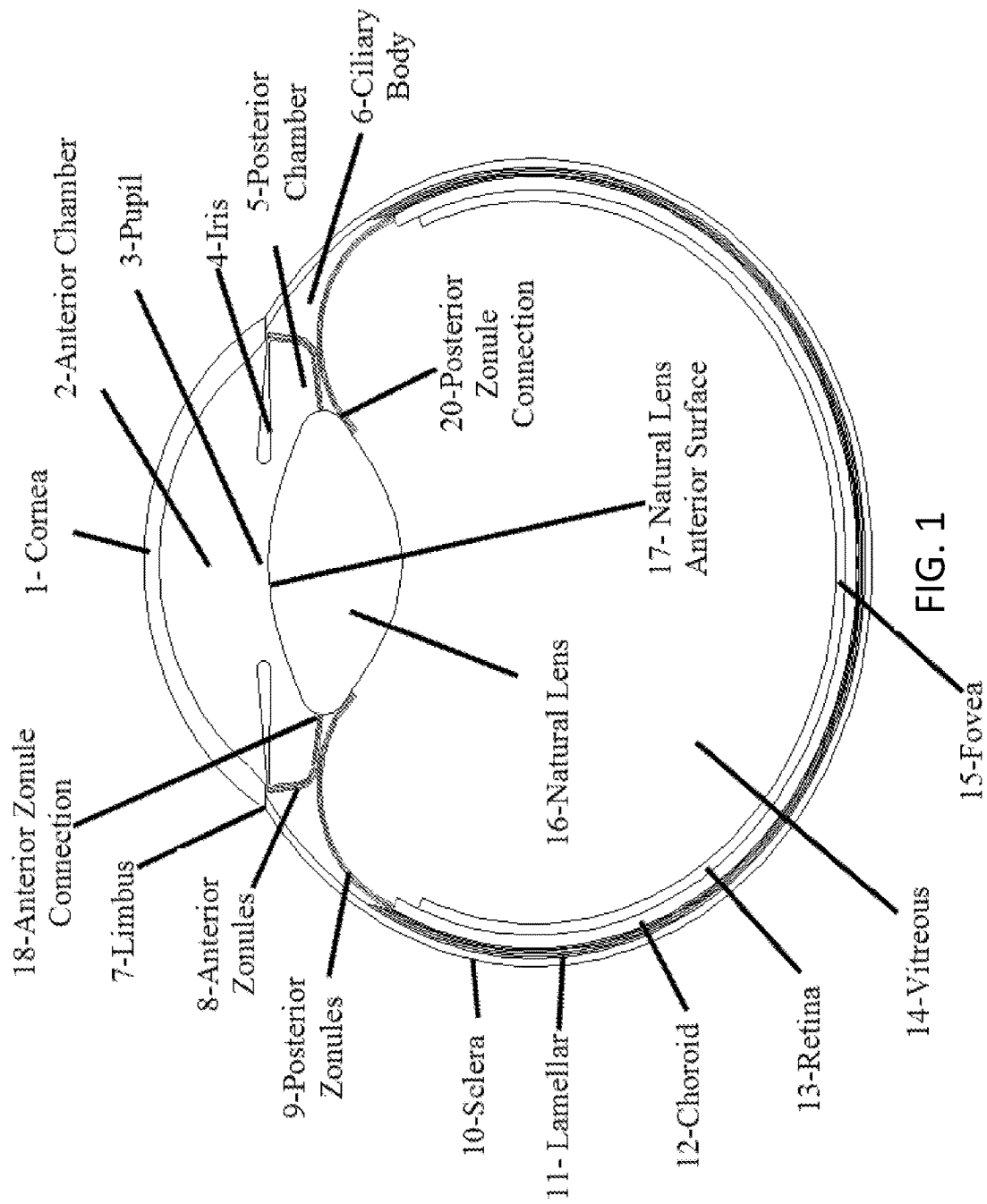
FIG. 1 is a diagram showing a cross-section of a human eye in the NEAR position where the natural lens is more globular. The zonules are shown passing through the ciliary body.
Figure 2:
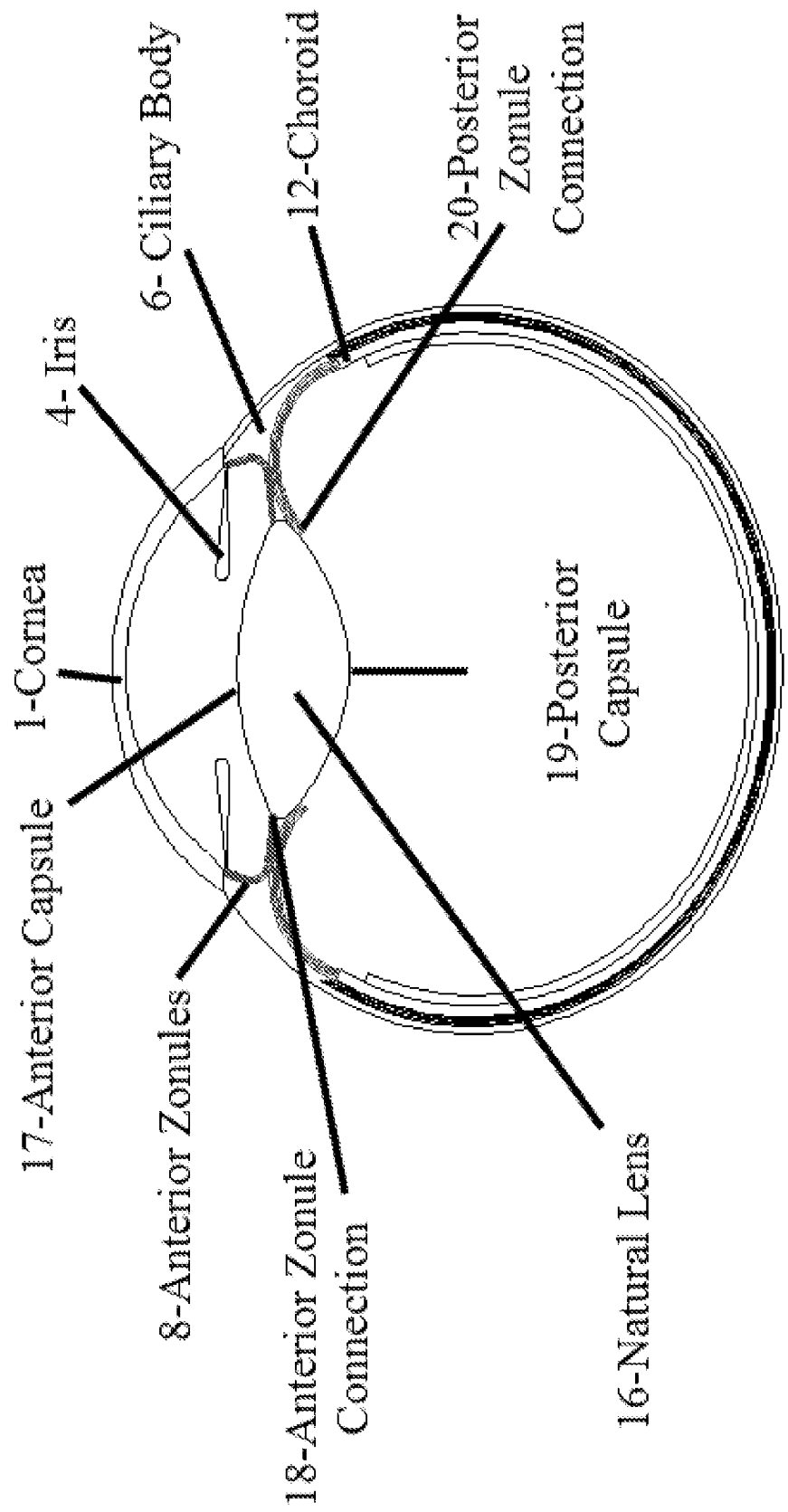
FIG. 2 is a diagram depicting the eye in the FAR position, with the natural lens flatter in shape.
Figure 3:
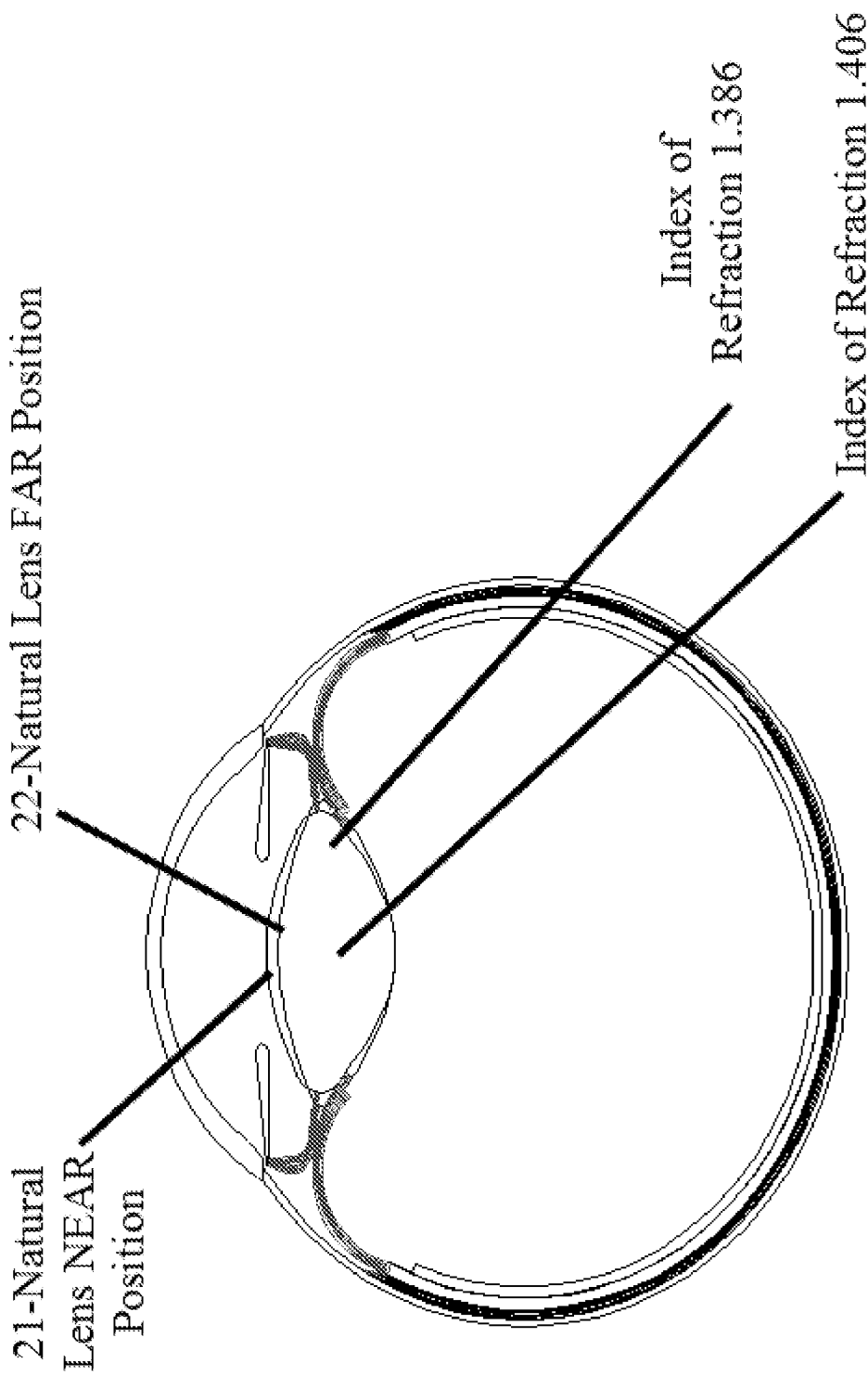
FIG. 3 is a diagram which compares the natural lens overlaid in the NEAR and FAR positions.
Figure 4:
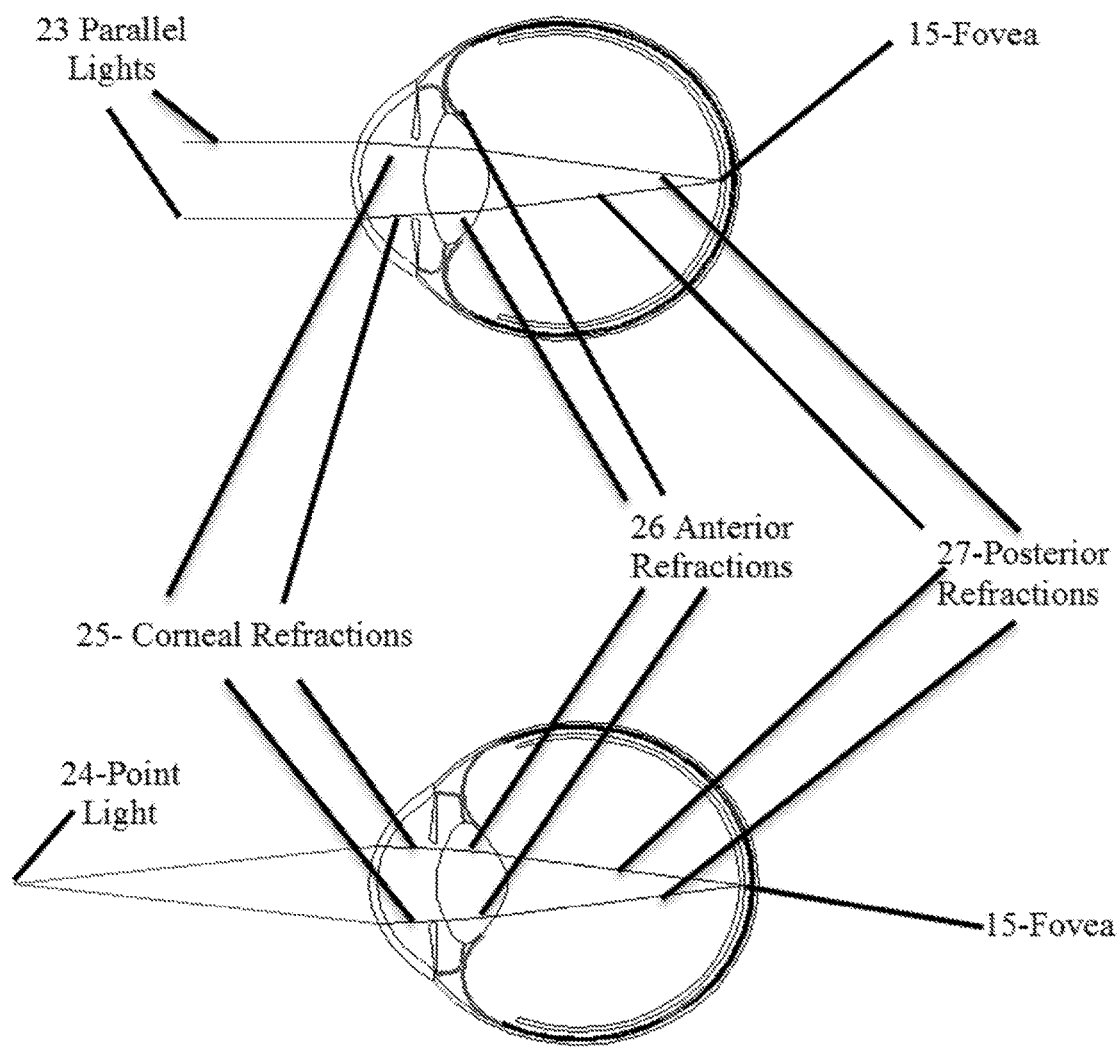
FIG. 4 is a diagram depicting a top cross-sectional view which shows parallel rays as would be the case when looking at distant objects approaching the eye from infinity; while the lower view shows light coming from a point source similar to reading.
Figure 5:
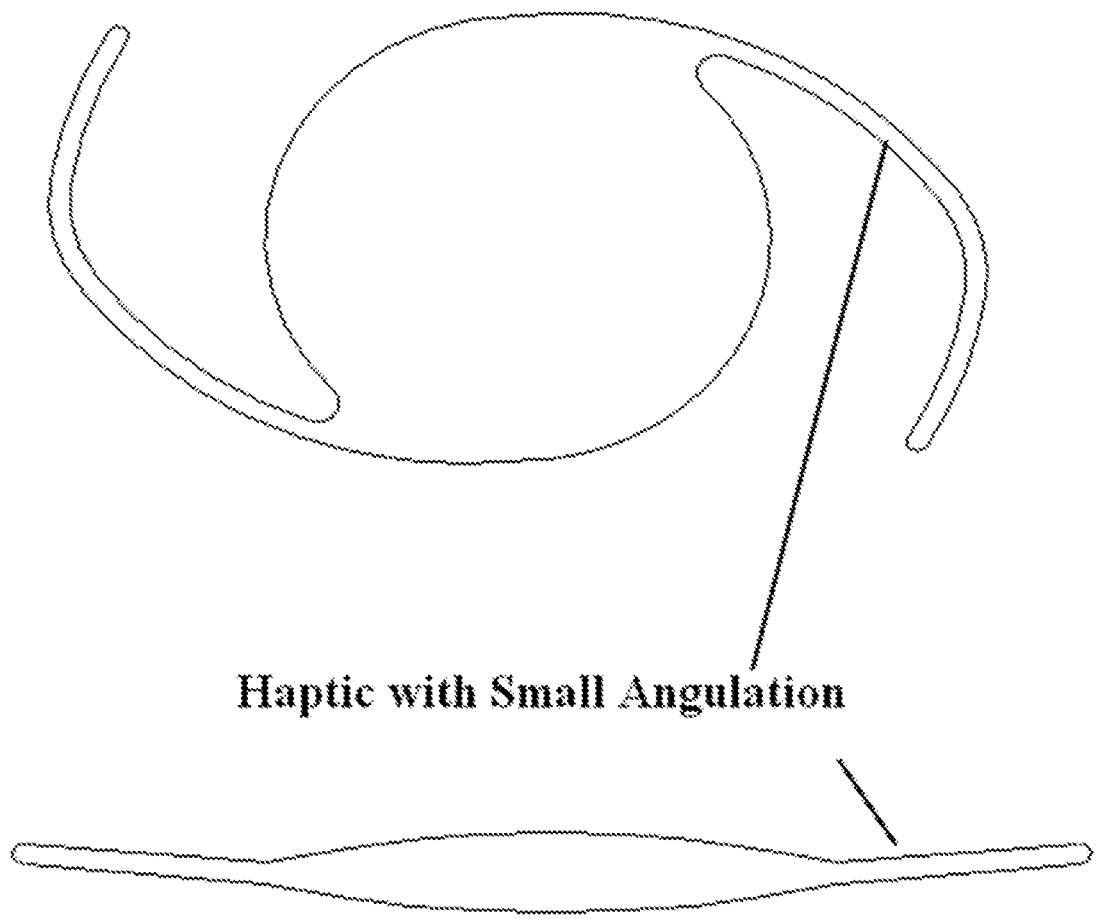
FIG. 5 is a diagram showing an older model lens which collapses the capsule tightly against the lens surfaces.

Reference will now be made in detail to various exemplary embodiments of the invention. It is to be understood that the following discussion of exemplary embodiments is not intended as a limitation on the invention. Rather, the following discussion is provided to give the reader a more detailed understanding of certain aspects and features of the invention.

Unless otherwise noted, definitions for ocular terminology included in this specification can be found in the Dictionary of Eye Terminology by Barbara Cassin and Melvin L. Rubin (ISBN 0-937404-44-6); Merriam Webster's Medical Dictionary (ISBN 0-87779-914-8); or American Heritage College Dictionary Fourth Addition (ISBN-13; 978-0-618-8359-9 ISBN-10; 0-618-83595-4). Other references that may provide background to the invention include Fundamentals of Optics—by Francis Jenkins & Harvey E. White (ISBN 0-07-032330-3) and Optical Engineering Fundamentals by Bruce H. Walker (ISBN-13: 978-0819475404; ISBN-10: 0819475408). Each of these references is hereby incorporated by reference in their entireties.

The following definitions may be useful for aiding in understanding of the invention.

Accommodation—Increase in optical power by the eye in order to maintain a clear image as objects are moved closer.

Accommodative Intraocular Lens—A lens that functions with the muscles (ciliary) of the eye to allow or force the intraocular lens to move anteriorly causing near objects to come into sharp focus.

Anterior Capsule—Front of the capsule enclosing the crystalline lens—Lies just behind the iris.

Anterior Capsular Opacification—Fogging of the anterior portion of the capsule remnant after cataract extraction and intraocular lens implantation. The fogging cells are attached to the capsule and not between the lens and capsule.

Anterior Capsulotomy—Surgically opening the front of the crystalline lens capsule in order to remove the crystalline lens.

Aphakia—Absence of the eye's crystalline lens.

Aqueous—Clear, watery fluid that fills the space between the back surface of the cornea and the front surface of the vitreous, bathing the natural lens. Produced by the ciliary processes. Nourishes the cornea, iris, and natural lens. Maintains intraocular pressure.

Aspheric Lens—A lens where the optical surfaces are not a portion of a sphere.

Capsular Bag—Bag-like lens capsule remnant remaining after cataract removal—Structure much like a thin lung or kidney. Used for placement of an intraocular lens.

Capsular Fixation—When an intraocular lens is held in position by insertion into the remnant of the natural lens capsule.

Capsule—See Capsular Bag—Elastic bag enveloping the eye's crystalline lens.

Capsulectomy—Surgical removal of part of the lens capsule.

Capsulorhexis—Opening in the lens capsule made in a continuous circular pattern for the removal of a cataractous natural lens and replacement with an intraocular lens.

Capsulotomy—Incision to open the natural lens capsule.

Cataract—Opacification or cloudiness of the crystalline lens of the eye to where enough light is retarded to decrease visual acuity.

Cataract Extraction—Removal of the cataractous natural lens of the eye.

Extracapsular—Method that leaves the rear portion of the lens capsule intact.

Intracapsular—Method that removes the entire lens capsule.

Ciliary Body—Circumferential tissue inside the eye composed of the ciliary muscle and ciliary processes. Controls the intraocular pressure and accommodation. Produces aqueous.

Ciliary Muscle—Portion of the ciliary body that connects to the zonules that attach to the natural lens capsule. Movement of the ciliary muscle causes movement of the zonules and in turn changes the shape of the natural lens allowing accommodation.

Ciliary Sulcus—Groove in the posterior chamber between the ciliary body and the iris.

Convex Lens—Lens that is thicker in the center than the edges.

Haptic—Non-optical portion of an intraocular lens that supports the lens against the affixation tissue of the eye (the inside surfaces of the capsule).

Hyperopia—Condition of the eye where the natural lens does not automatically compensate by increasing the power needed by the patient for clear vision. The image focuses behind the retina.

Hyperopic—Farsighted—Objects focus behind the retina.

Intraocular lens (IOL)—An artificial lens placed inside the eye. Often used after cataract surgery. Also used to correct for myopia or hyperopia.

HEMA (hydroxy-ethyl-methacrylate)—Plastic polymer used to make soft contact lenses. A chemical derivate of polymethylmethacrylate.

Multi-focal—Optical surface where light rays entering the surface at different radial locations come to focus at different points.

Near Sightedness—Myopia—Light rays from distant objects come to focus in front of the retina.

Polymethylmethacrylate (PMMA)—Hard lens material with little flexibility. Was the initial material used to make intraocular lenses. While newer hydrophilic and hydrophobic materials are being used, PMMA is still used to manufacture intraocular lenses.

Silicone—Soft contact lens and intraocular lens material that is soft without maintaining hydration. Can be injection molded.

Milling Machine—Used in lens production to shape the haptics into spring-like structures to hold the optic in position.

Post Capsular Opacification, PCO—Fogging of the posterior portion of the capsule remnant after cataract extraction and intraocular lens implantation. The fogging cells are attached to the capsule and not between the lens and capsule.

Posterior Capsulotomy—An incision into the capsule behind an intraocular lens. Opens the capsule allowing light to pass through when the capsule has opacified.

Posterior Chamber Intraocular Lens (PCIOL)—An artificial lens implanted into the space behind the iris. Most often the lens is placed inside the capsule remnant after cataract extraction.

Presbyopia—Refractive condition in which there is a diminished power of accommodation. Arises from a loss of elasticity of the crystalline lens. Occurs with aging.

Pseudophakia—State of having an intraocular lens implanted. Taking the place of the eye's natural lens.

Trabecular Meshwork—Mesh-like structure inside the eye at the iris-scleral junction of the anterior chamber angle. Filters aqueous fluid and controls its flow out of the eye.

Vitreous—Transparent colorless gelatinous mass that fills the rear two-thirds of the eye ball, between the natural lens and the retina.

Zonules—Radially arranged fibers that suspend the lens from the ciliary body and hold it in position. During accommodation movement of the ciliary body causes the forces on the zonules to change, which in turn changes the shape of the natural crystalline lens.

Figure 6:
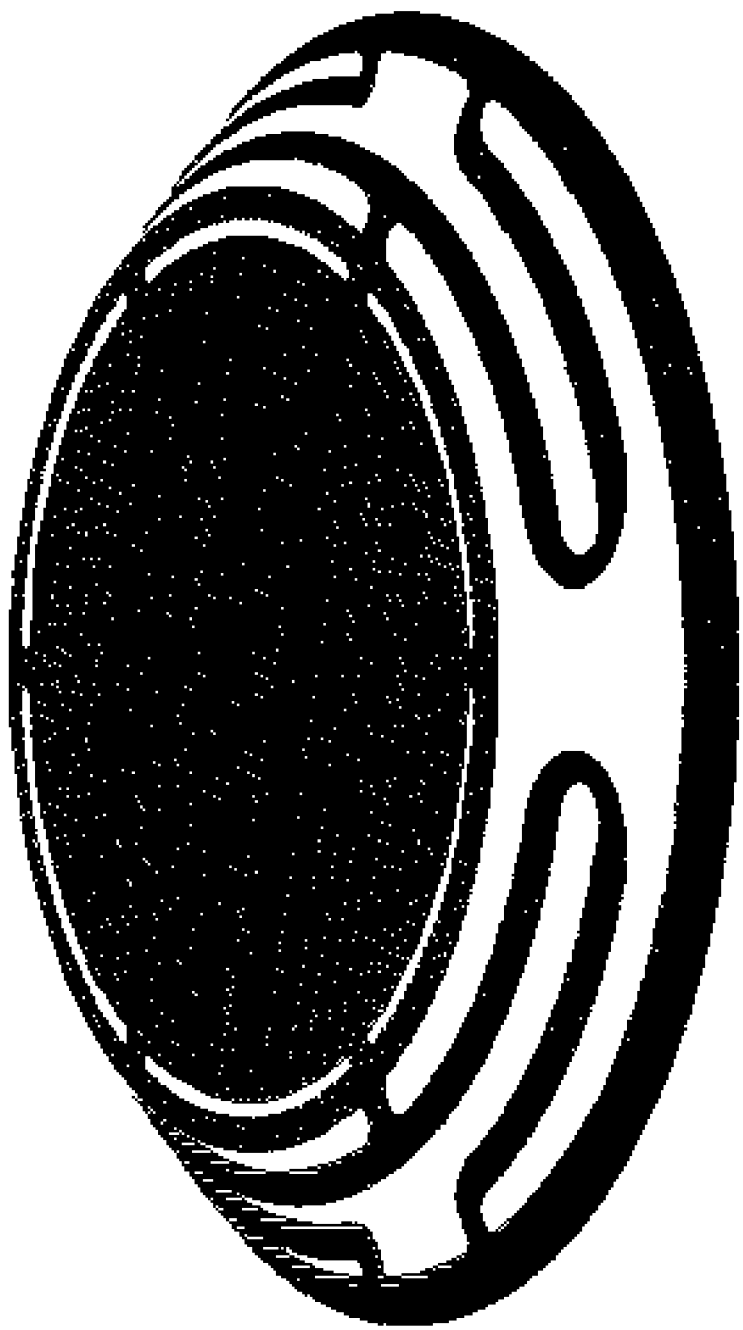
FIG. 6 is a diagram showing a 3-dimensional perspective view of a preferred embodiment of the invention.

Turning now to the figures, FIG. 6 shows an embodiment of a 3-dimensional intraocular lens (IOL) in the NEAR position with over one millimeter of movement. Additional accommodation from differential pressures between the aqueous and vitreous is also possible. The lens can be manufactured using high precision lathes available from multiple companies located within the United States. Manufacturing using 3D printing may also be considered for all or a portion of the device, such as the support structure for the lens, including the annuluses, ribbons, and/or tabs. In any embodiment, the lens may be manufactured from materials such as polymethylmethacrylate (PMMA), silicone, hydrophobic acrylate, hydrophilic acrylate and collamer, and the like.

Figure 7:
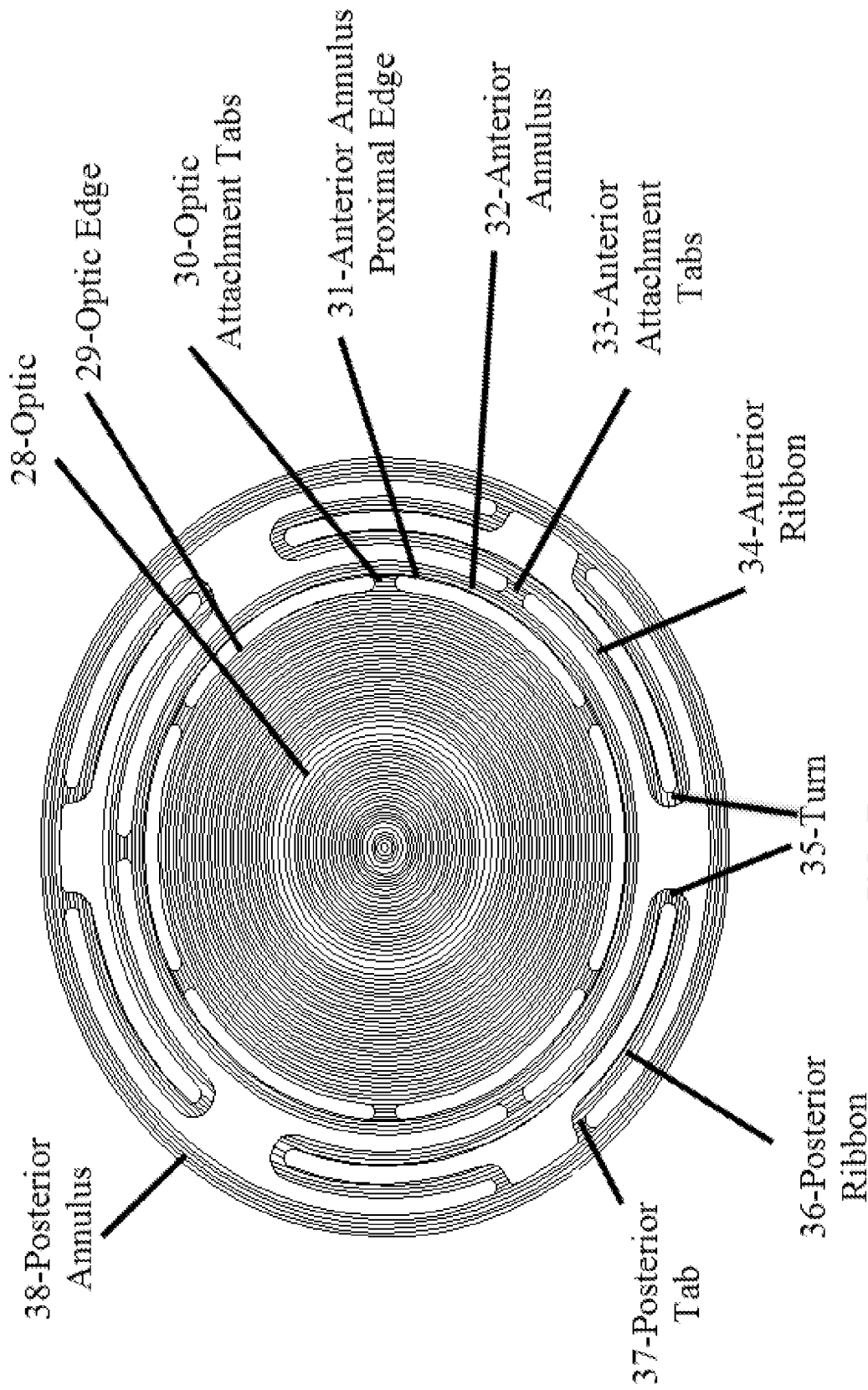
FIG. 7 is a diagram showing a top planar view of a preferred embodiment of the invention.
Figure 8A:
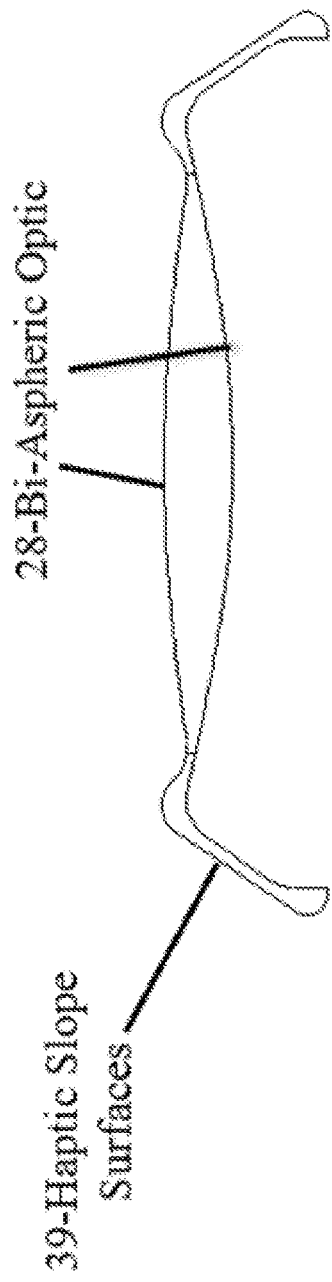
FIG. 8A is a diagram showing a cross-sectional view of a preferred embodiment of the invention prior to cutting the haptic ribbons.
Figure 8B:
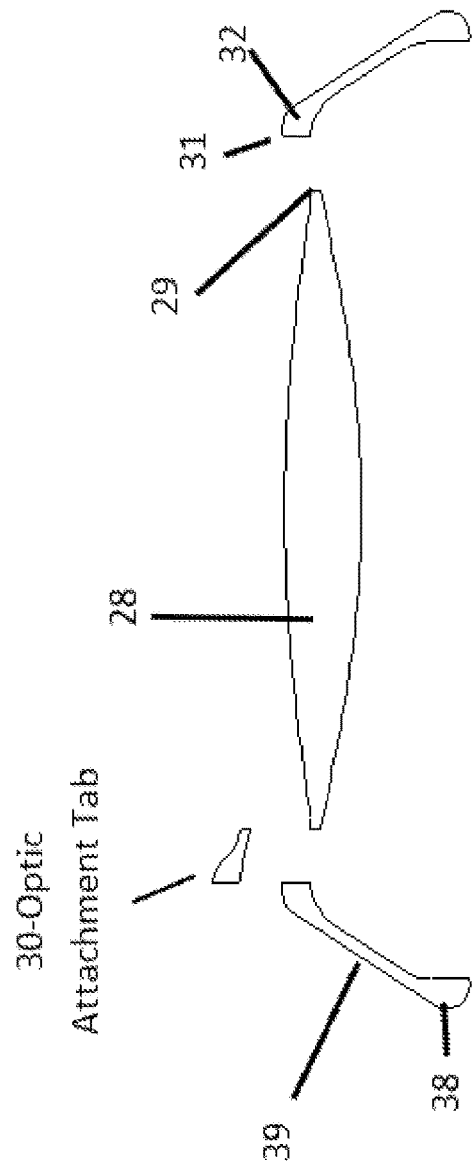
FIG. 8B is a diagram showing a view through the centerline of FIG. 7 showing the opening between the optic edge (29) and the anterior annulus proximal edge (31).

Referring to FIGS. 7, 8A, and 8B, a top planar view of an embodiment of the 3-dimensional lens is shown in FIG. 7 with the optic (28) shown inside or surrounded by the anterior annulus (32). The optic edge (29) and the anterior annulus proximal edge (31) are connected via spaced attachment tabs (30). The attachment tabs can be equally spaced around the annulus and/or lens or can be spaced at any interval. FIGS. 8A and 8B provide cross-sectional views showing that the tabs (30) are the same thickness as the end of the member to which they are to be connected; therefore, the thickness varies across the cross-sections. For example, as shown, tab (30) has a greater thickness at the end connected with anterior annulus proximal edge (31) and a thinner thickness at the end connected with optic edge (29). In FIG. 8B, tab (30) is shown separated from the device to illustrate it in isolation. Distally attached to the anterior annulus is the haptic slope (39), which is initially cut into a conical section. FIG. 7 shows anterior attachment tabs (33) are cut into the haptic slope connecting the anterior annulus to the anterior ribbon (34). The tabs are located at the center of the anterior ribbons and for the preferred embodiment the ribbons are cut concentric to the anterior annulus. When a distance to obtain the desired flexibility is achieved the anterior ribbons (35) turn 180 degrees becoming posterior ribbons (36) and through tabs (37) attach to the posterior annulus (38). The haptic slope is cut to allow each member between the optic and posterior annulus to come to the FAR position with separation between each component as to allow maximum movement of the lens optic without any lateral movement to place stress on the capsule remnants. In the NEAR position there is a small force from the natural lens capsule holding the lens in position. In the FAR position the lens is squeezed posteriorly. Individually the anterior and posterior ribbons (34, 36) would function much like a cantilevered beam (diving board); however, when connected (35) the function changes to be more like two layers of a leaf or complex spring. Within the eye the lens is designed to be at rest in the NEAR position. FIG. 8B shows an embodiment of a bi-convex-bi-aspheric optic (28) which allows for a smooth surface and a very thin profile at the center of the lens, making the overall cross-section smaller, which reduces the incision size needed for implantation. The aspherical design can allow adjustments of the optic to remove aberrations from the eye. The anterior annulus (32) is slightly higher than the apex of the anterior optic, which reduces the possibility of warpage via contact with the anterior capsule. The differential height plus the space between the optic edge and the anterior annulus allows clearance to provide aqueous flow for hydration inside the capsule. With 3-dimensional lenses designed for accommodation the natural lens capsular remnants are critical to prolonged anterior-posterior movement. The aqueous carries the needed nutrients to the structures that do not contain blood vessels. The anterior annulus proximal surface (31) to the optic has a surface exposed to the anterior capsule that will remove some PCO generated via the capsule epithelium. The PCO removed from the epithelium is saturated with aqueous for removal from the eye as the aqueous is removed via the trabeculum.

Figure 9A:
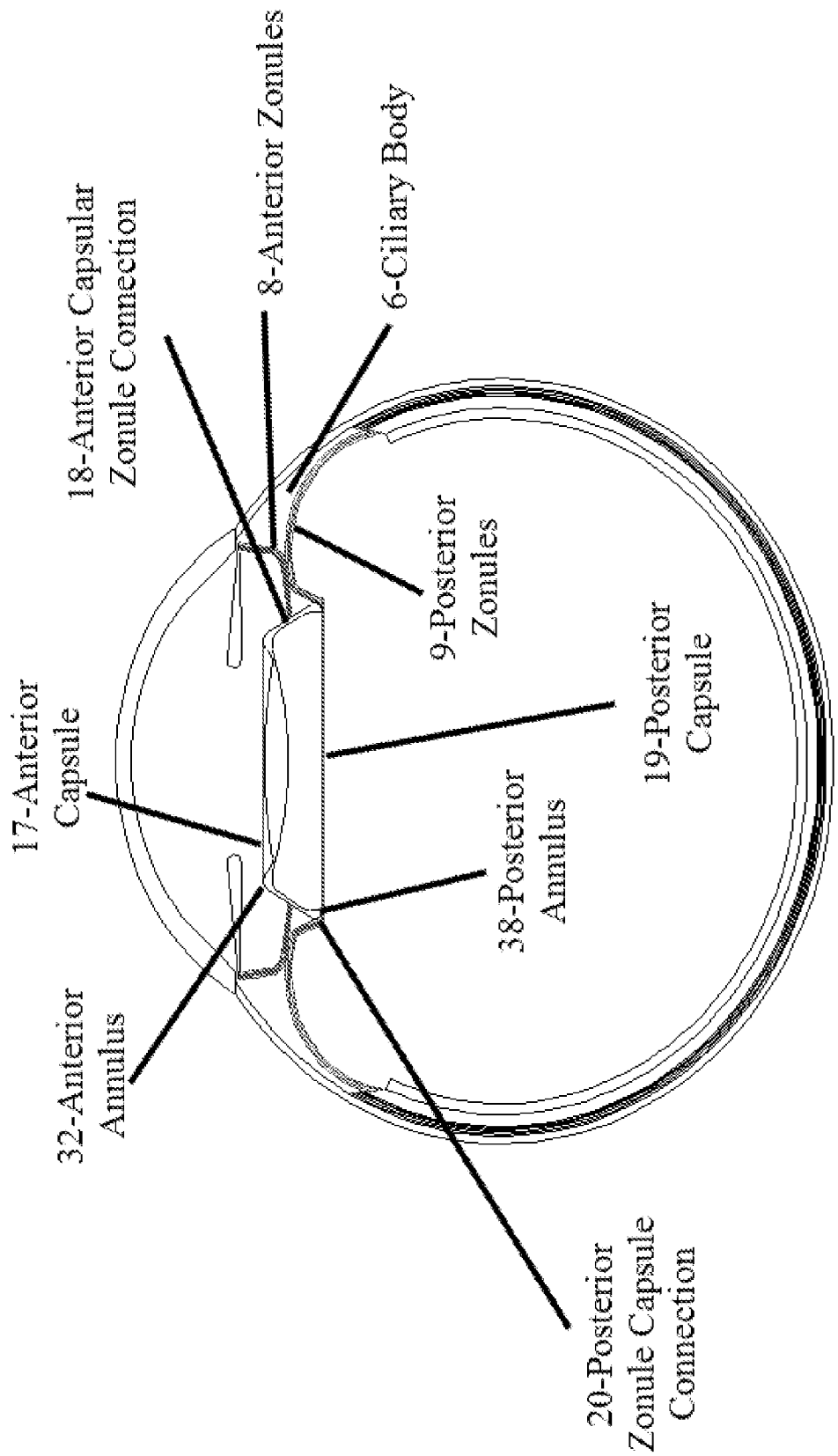
FIG. 9A is a diagram showing a cross-sectional view of an eye showing a preferred embodiment of the invention.
Figure 10:
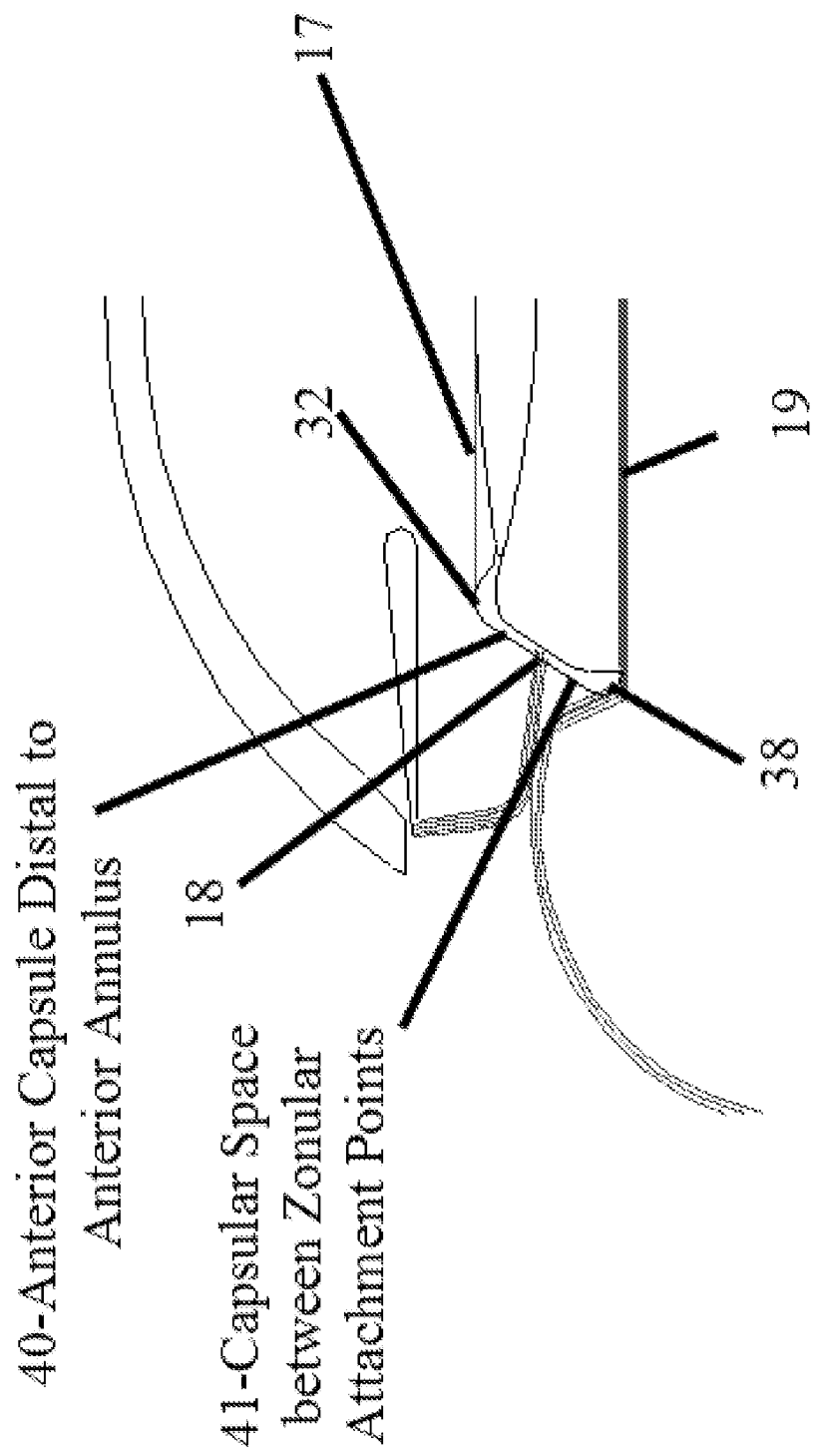
FIG. 10 is a diagram showing a cross section of a portion of the view of FIG. 9.

Turning to FIGS. 9A and 10, the anterior capsule 17 of the natural lens stretches against the anterior annulus (32) with a portion of the capsule wrapping around the annulus. The posterior capsule (19) stretches against the posterior annulus (38) at or near the capsular-zonular junction (20). Both surfaces stretch taut and tangentially to the respective annuluses pulling the surfaces flat and holding the lens in position. The space between the attachment points (41) is also tight in the near position and squeezed to occupy minimal space in the far position. While most lenses are designed for a polar capsular circumference of 21 millimeters; some eyes are smaller. If the eye has a smaller polar circumference, embodiments of the present invention automatically adjust to the size of the capsule for NEAR vision. Some potential accommodation will be lost; however, significant accommodation should still be available as only a small portion of the potential movement should be needed for sizing. The lens in the preferred embodiment is designed to place the posterior annulus (38) at the 20-Posterior Zonule Capsule Connection, which gives additional strength as both surfaces weave together increasing the strength. The lens is held in the capsule by the annuluses with some tension along the ribbons. Only a small amount of tension is necessary to hold the lens in the NEAR position.

As shown in FIGS. 9A and 10, when viewing NEAR objects the ciliary processes remove tension on the zonules and the pressure in the vitreous is slightly higher than the pressure in the aqueous; therefore, the lens optic rests in the most anterior position.

Figure 9B:
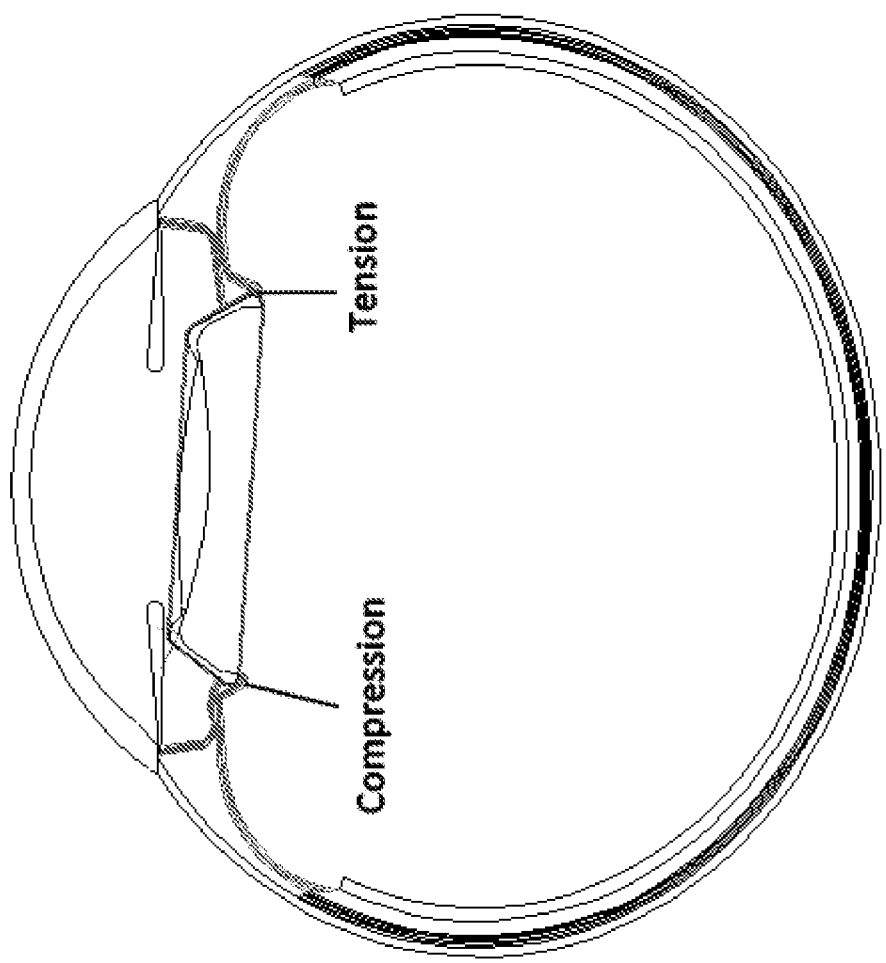
FIG. 9B is a diagram showing a cross-sectional view of an eye showing a preferred embodiment of the invention with the lens offset to the left side.

FIG. 9B shows a cross-sectional view with the lens offset to the left side which puts the zonules in that section under compression and the zonules 180 degrees away in tension or at least less compression. In addition, the capsule between the zonule attachment points (41) is stretched tighter on the compression side resembling an arcuate. The combination of the forces will center the lens.

Figure 11:
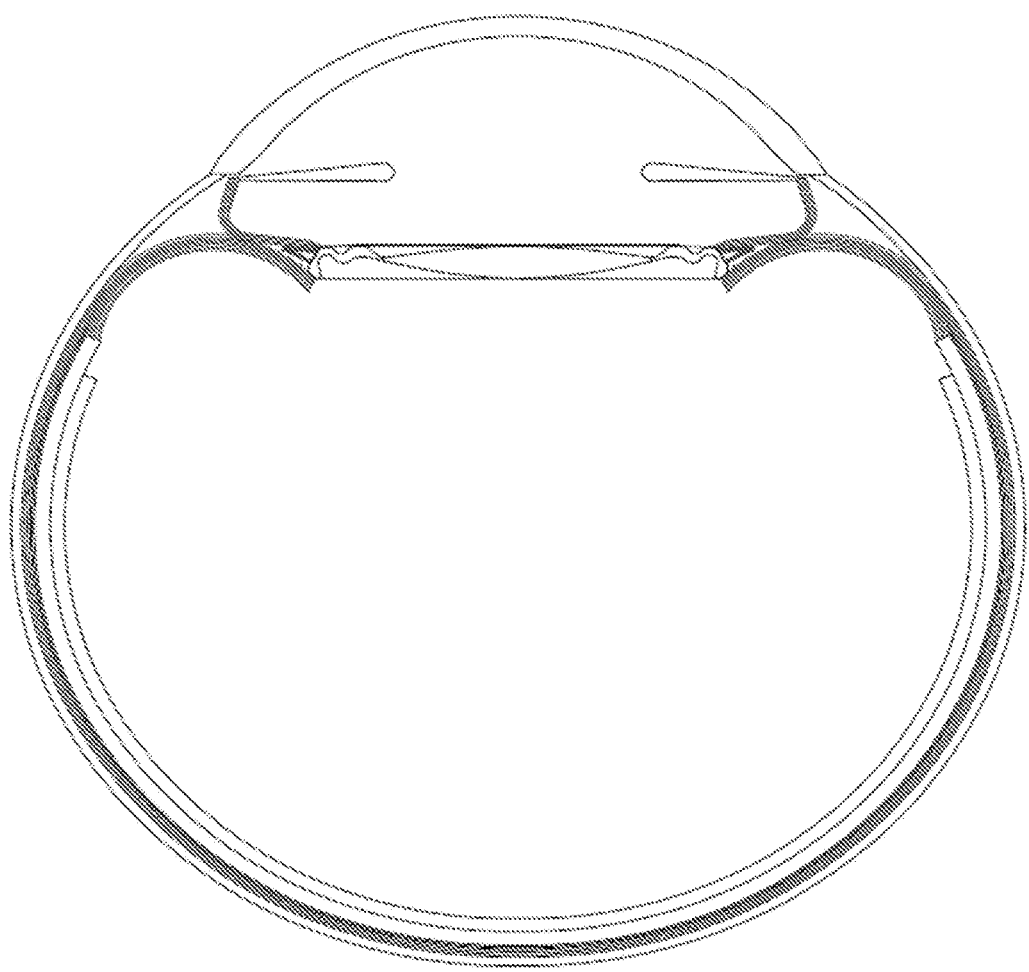
FIG. 11 is a diagram showing a preferred embodiment of the invention implanted and squeezed into the FAR position.
Figure 12:
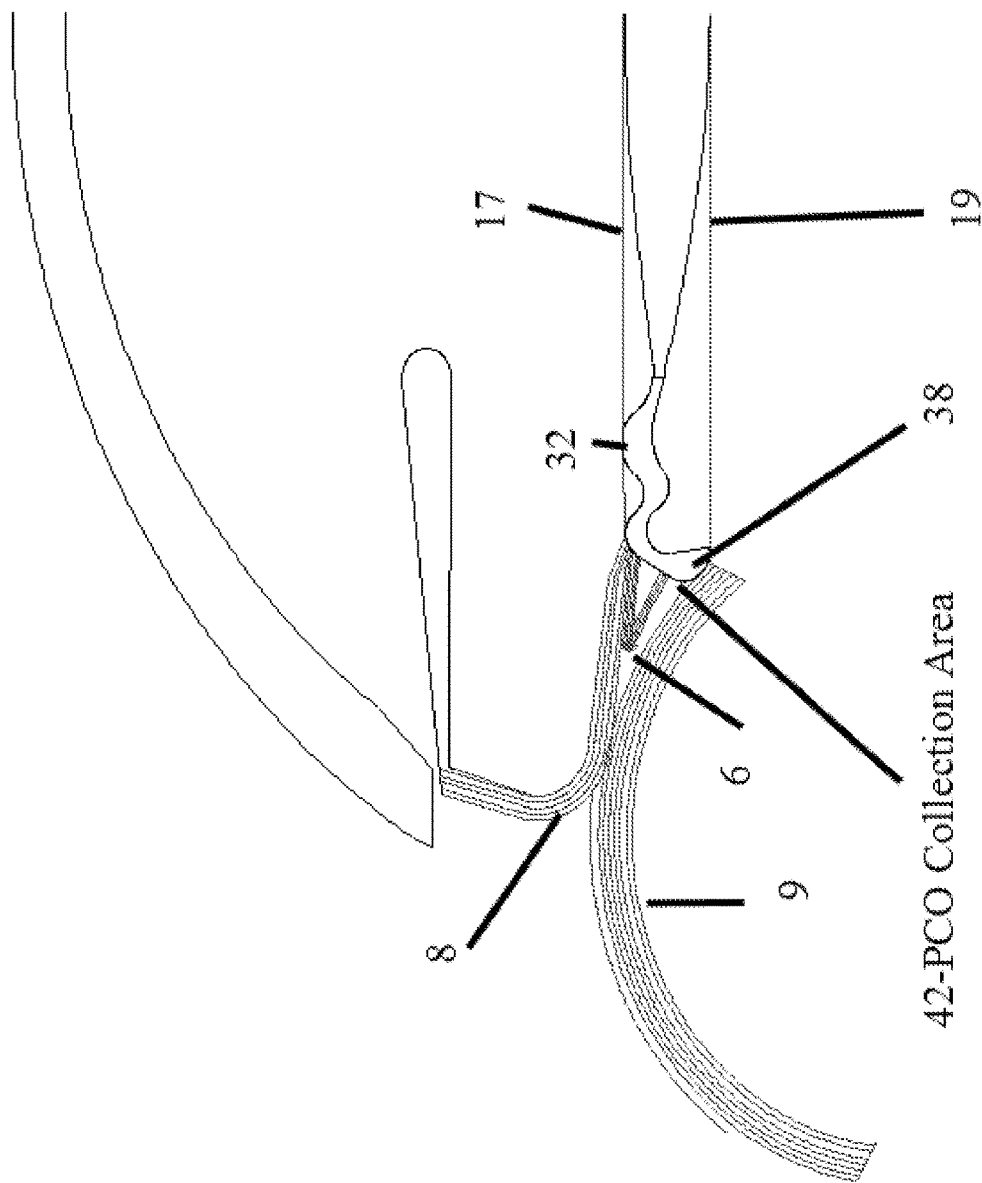
FIG. 12 is a diagram showing a cross section of a portion of the view of FIG. 11.

As shown in FIGS. 11 and 12, when viewing FAR objects the ciliary processes place tension on the anterior and posterior zonules stretching the natural lens capsule which applies an anterior/posterior force vector across the two annuluses which is transferred through the tabs to the ribbons collapsing the IOL optic into the FAR position. The expected distance from the NEAR to the FAR position due to the ribbons functioning as a complex spring is over one millimeter. The differential vitreous/aqueous pressure is expected to provide additional movement. Since the annuluses are stretched tight there is no relative motion between the capsule and annuluses; therefore, there is no frictional force, which if present could erode the capsule. When moving from NEAR to FAR focus it is apotheosized, the lens will move posteriorly stopping at emmetropia even though the lens has not hit a hard stop. If the cataract surgeon leaves the patient slightly hyperopic the force is expected to stop at the desired position of the lens to achieve emmetropia.

After cataract surgery the fibers that caused the over population of the natural lens cavity will continue proliferation. If left unchecked they will accumulate creating capsular opacification.

The cells are generated along the epithelium of the anterior surface of the natural lens (17) (see FIG. 10), which is also resting against the anterior annulus (32). As cells move distally from the prime meridian to the anterior annulus proximal edge (31) (see FIG. 8B) many of the cells will be scraped into the aqueous. Once the cells are surrounded by aqueous there is not a tendency for reattachment to the intraocular lens or the capsule. With movement of the optic and anterior annulus either posteriorly or anteriorly turbulence is created allowing additional PCO to be removed from the anterior annulus.

Once the PCO fibers are saturated with aqueous they do not have an affinity to reattach; therefore, they are carried out of the eye through the trabecula meshwork and carried back to the blood stream.

Cells generated distal to the anterior annulus proximal edge will continue proliferation and migrate toward the posterior capsule (19) (see FIG. 10). This is true in both the NEAR and FAR positions.

In the NEAR position the anterior and posterior ribbons (34, 36) (see FIG. 7) are part of the haptic slope (39) (see FIG. 8) allowing the capsule to rest against it. There is little or no force between the capsule and ribbons, so limited PCO is removed. In the FAR position the anterior capsule distal to the anterior annulus (40) and the capsular space between the zonule attachment points (41) (see FIG. 10) is not always in contact with the lens haptic; therefore, cells will migrate toward the posterior capsule (19) (see FIG. 12) and collect along the posterior annulus (38). Cells not scraped from the lens will arrive at the PCO Collection Area (42) and be sandwiched between the posterior capsule and the annulus. With eye movement from FAR toward the NEAR position the cells will be initially squeezed from the PCO collection area ejecting many into the aqueous for saturation. If enough PCO is collected around either annulus a PCO annulus can form. The squeezing from FAR to NEAR vision will rupture the PCO annulus, causing a portion to separate and become saturated with aqueous. The process will be repeated with each movement of the eye. In the FAR position, inside the capsule, there is approximately one-third of the volume of aqueous as there is in the NEAR position; therefore, aqueous (with fibrous cells) is pumped out of the capsule.

Lenses can be manufactured from hydrophobic or hydrophilic materials. One company with such materials is Contamac (Saffron Walden, United Kingdom). Historically, their main product for intraocular lenses has been a hydrophilic material made of a copolymer of hydroxyethyl methacrylate with a 26% water content. The material squeezes into a small cross-section allowing a small incision and opening instantly upon departure from an injector. The surgeon can immediately position the lens. Prior to hydration the hydrophilic materials are brittle. The water content in hydrophobic lenses is added during the raw material manufacture making the material soft. The soft materials usually have to be cooled or frozen to allow lathe turning, while the hydrophilic materials can be lathe turned, then hydrated. Contamac also has an 18% water content material that is stiffer and not popular because the material opens slowly causing the surgeon delay for centration. With a 3 dimensional design as is the current invention the lens can be manufactured using stiffer or lower water content material then squeezed into a small profile and grasped with forceps for implantation. The lens will open as fluid is absorbed and the materials warm to body temperature. As long as the lens has a round posterior surface such as is provided by an annulus and has a vertical force component the lens will move with each change of the eye from FAR to NEAR until the lens is fully centered. With slight decentration the lens will re-center with each accommodation cycle. See, for example, FIG. 9B. Any material with mechanical strength and optical quality that is compatible with human eye tissue can be used.

Figure 13:
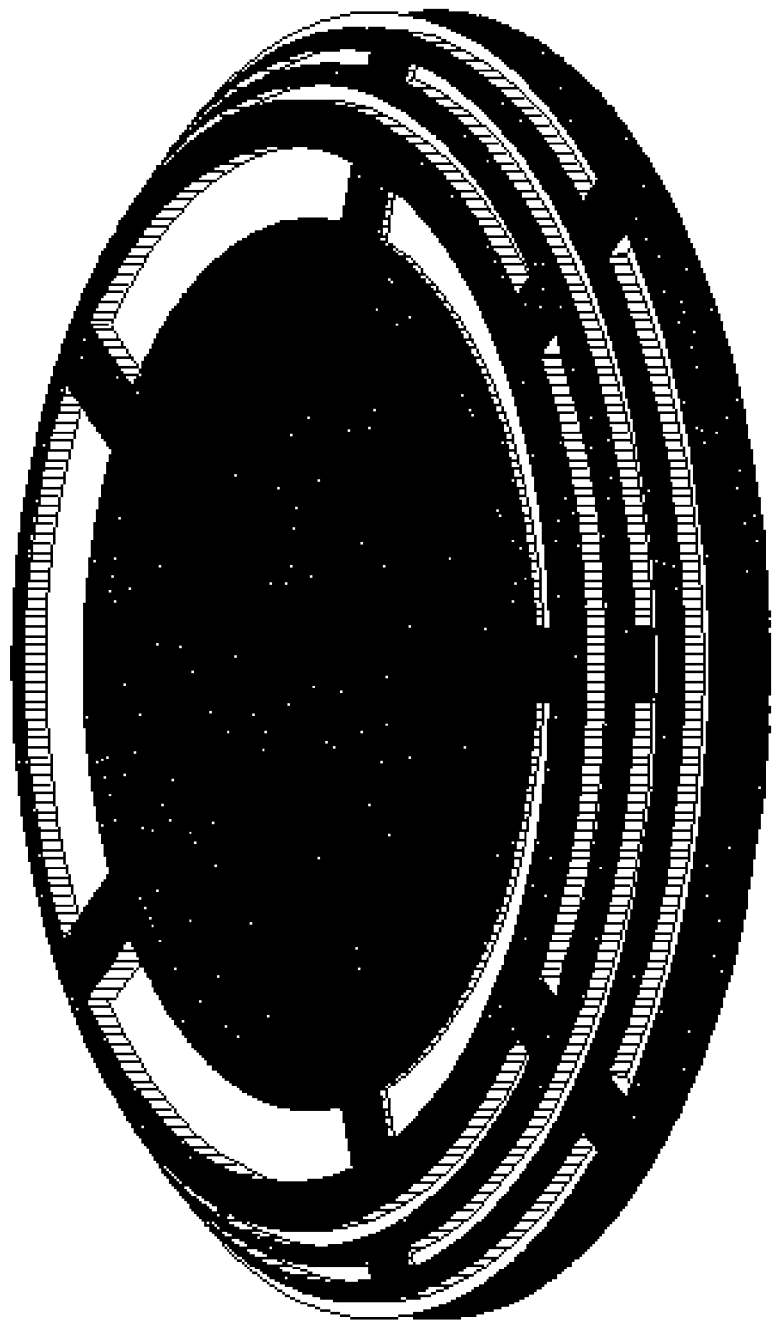
FIG. 13 is a diagram showing an embodiment of the invention with multiple annuluses.

FIG. 13 shows an alternate design replacing the cantilevered section with one or more additional annuluses. The optic can be the same as the preferred embodiment with tabs connecting to the anterior annulus and the anterior annulus apex resting in a plane slightly higher than the apex of the lens optic. There can be additional annuluses concentric to the anterior annulus. In any embodiment described in this specification, there can be from 1-20 annuluses, such as 1, 2, 3, 4, 5, 6, 7, 8, 9, or 10 annuluses. The annulus below the anterior annulus is large enough to allow the anterior annulus outside diameter to fit inside the second annulus. The relationship continues with the posterior annulus inside diameter larger than the outside diameter of the previous annulus. The design assumes the material is more flexible and most likely having less mechanical strength. The design is more desirable for softer materials. The number of annuluses will be determined by the strength of the material and the space available.

The present invention has been described with reference to particular embodiments having various features. In light of the disclosure provided above, it will be apparent to those skilled in the art that various modifications and variations can be made in the practice of the present invention without departing from the scope or spirit of the invention. One skilled in the art will recognize that the disclosed features may be used singularly, in any combination, or omitted based on the requirements and specifications of a given application or design. When an embodiment refers to "comprising" certain features, it is to be understood that the embodiments can alternatively "consist of" or "consist essentially of" any one or more of the features. Other embodiments of the invention will be apparent to those skilled in the art from consideration of the specification and practice of the invention.

It is noted in particular that where a range of values is provided in this specification, each value between the upper and lower limits of that range is also specifically disclosed. The upper and lower limits of these smaller ranges may independently be included or excluded in the range as well. The singular forms "a," "an," and "the" include plural referents unless the context clearly dictates otherwise. It is intended that the specification and examples be considered as exemplary in nature and that variations that do not depart from the essence of the invention fall within the scope of the invention. Further, all of the references cited in this disclosure are each individually incorporated by reference herein in their entireties and as such are intended to provide an efficient way of supplementing the enabling disclosure of this invention as well as provide background detailing the level of ordinary skill in the art.

The invention claimed is:

1. An intraocular lens comprising:
an optic;
a haptic supporting the optic and comprising an outer annulus and an inner annulus, wherein the outer annulus has a larger radius than a radius of the inner annulus;
wherein the inner annulus is in communication with the outer annulus by way of a plurality of tabs and a plurality of ribbons, and a plurality of intermediate annuluses, wherein each of the ribbons comprises an arcuate bend.

2. The intraocular lens of claim 1, wherein the inner annulus is in communication with the optic by way of a plurality of tabs.

3. The intraocular lens of claim 1, wherein the inner annulus is in communication with the outer annulus by way of at least one intermediate annulus, and tabs connecting the inner annulus to the at least one intermediate annulus, and tabs connecting the at least one intermediate annulus to the outer annulus.

4. The intraocular lens of claim 3, wherein the at least one intermediate annulus comprises two intermediate annuluses.

5. The intraocular lens of claim 1, wherein the arcuate bend is a 180 degree bend.

6. The intraocular lens of claim 1, wherein the haptic is flexible and capable of disposing the optic in a position between the inner annulus and the outer annulus.

7. The intraocular lens of claim 1, wherein the optic is bi-convex.

8. The intraocular lens of claim 1, wherein the optic is bi-aspheric.

9. The intraocular lens of claim 1, wherein the haptic slopes outwardly from the inner annulus to the outer annulus.

10. An intraocular lens comprising:
an optic;
a haptic in communication with the optic, comprising:
a first annulus;
a second annulus;
a plurality of tabs connecting the optic and the annuluses;
wherein a cross-section of the intraocular lens along a plane perpendicular to a diameter of the intraocular lens reveals that the haptic is sloped; and
wherein the first annulus is in communication with the second annulus by way of at least one intermediate annulus, and tabs connecting the first annulus to the at least one intermediate annulus, and tabs connecting the at least one intermediate annulus to the second annulus.

11. The intraocular lens of claim 10, wherein the haptic is flexible and capable of disposing the optic in a position between the first annulus and the second annulus.

12. The intraocular lens of claim 10, wherein the optic is bi-convex.

13. The intraocular lens of claim 10, wherein the optic is bi-aspheric.

14. An intraocular lens comprising:
an optic;
a flexible haptic comprising an inner annulus and an outer annulus with additional annuluses, tabs, and cantilevered structures between the inner annulus and the outer annulus configured to provide flexibility to the haptic from a compressed state to a relaxed state;
wherein when the haptic moves from a relaxed state to a compressed state, the inner annulus moves posteriorly toward the outer annulus to increase the strength of distant vision; and
wherein when the haptic moves from a compressed state to a relaxed state, the inner annulus moves anteriorly to provide for stronger near vision.

15. The intraocular lens of claim 14, wherein during use by a subject the annuluses, tabs, and cantilevered structures function as a spring such that the annuluses are at a maximum separation when the subject is viewing near objects and at a minimum separation when the subject is viewing far objects.

16. The intraocular lens of claim 14, wherein the optic is bi-convex.

17. The intraocular lens of claim 14, wherein the optic is bi-aspheric.

18. The intraocular lens of claim 14, wherein the cantilevered structures comprise a plurality of ribbons.

19. The intraocular lens of claim 18, wherein each of the ribbons comprises an arcuate bend.

20. The intraocular lens of claim 19, wherein the arcuate bend is a 180 degree bend.

* * * * *